United States Patent Office

Plant Pat. 1,895
Patented Jan. 5, 1960

1,895

GRAPEVINE

Wayne Thornburg, Litchfield Park, Ariz.

No Drawing. Application April 16, 1959
Serial No. 806,990

1 Claim. (Cl. 47—62)

The present invention relates to a new and distinct grapevine which was discovered by me as a sport of the variety known as "Cardinal" (unpatented), said discovery having occurred on my cultivated property near Litchfield Park, Arizona.

At the time of my discovery of this sport, I was growing in one of the vineyards on my property referred to above some 61,406 "Cardinal" grapevines which had been planted by me as unrooted cuttings. During the maturing season some 4 years later, I found among these vines one particular vine (and only one) which appeared to be maturing substantially earlier than all of the other vines. Continued observation of this particular vine for two additional seasons showed that its earlier-maturing behavior was repeated, and I concluded therefrom that one of the originally planted "Cardinal" cuttings had sported.

Accordingly, I took steps to carefully preserve the sport, keep it under observation, and to asexually reproduce the same by cuttings, and also from nursery rootings from cuttings, which were planted by me on my aforementioned property. All of these reproductions have consistently confirmed the earlier-maturing habit of the original sport, and that the fruit thereof is ready for picking and marketing from about 10 days to 2 weeks earlier than that of the regular "Cardinal" variety. Except for the earlier-maturing habit, my new sport is substantially identical in all respects to the well-known "Cardinal" parent variety, and therefore need not be described in detail or illustrated herein.

However, for the convenience of those not fully acquainted with the regular "Cardinal" variety, I will briefly explain that it was originated at the United States Horticultural Field Station at Fresno, California, as more particularly described and illustrated in Circular No. 882, published August, 1951, by the United States Department of Agriculture. As stated therein, the "Cardinal" variety was one of several that resulted from a grape breeding program begun in 1923 at Fresno to produce table grape varieties of more attractive size and color, having better eating qualities and which would extend the season either as earlier-maturing types, or as late-storage types. The "Cardinal" variety filled the need for a type having earlier maturity, good eating quality, and attractive appearance.

My new sport still further extends the early-maturing and early-marketing range, and thus is endowed with a highly valuable characteristic from a commercial standpoint.

The parent "Cardinal" variety was first introduced in 1946, and resulted from a cross of "Flame Tokay" × "Ribier," both unpatented varieties. It was the earliest commercial vinifera variety then known. Its chief characteristics are as follows:

Vine: Medium vigorous; very productive of cluster forms; 3 or 4 clusters often produced on each growing shoot, making it advisable to thin off some when the shoots are from 12 to 18″ long, in the pre-blossom stage, in order to produce fruit of superior size and quality. Canes—short to medium-length inter-nodes; color—reddish brown.

Foliage: From 3- to 5-lobed; margin deeply dentate.

Flowers:

*Buds*—Medium late.

*Blossoms*—Self-fertile; upright stamens; opening early.

Fruit: Borne in medium large clusters; from conical to cylindrical; not broadly shouldered; ripening very early; firm.

*Size*—Large; 1″ or more in diameter.

*Shape*—From nearly spherical to slightly oblate.

*Skin*—Medium tough. Color—rich, dark red, with grayish bloom.

*Pulp*—Firm.

*Seeds*—Relatively few in number, ranging from 1 to 4, but usually 2 per berry; rather soft.

Shipping quality: Excellent.

Eating quality: Excellent; slight muscat flavor noticeable when fully matured.

I claim:

A new and distinct variety of grapevine, substantially as herein shown and described, characterized particularly as to novelty by its general similarity to the variety "Cardinal" (unpatented), but being distinguished therefrom by a maturing habit averaging from 10 days to 2 weeks earlier than "Cardinal," with consequent corresponding earlier marketability of the fruit.

No references cited.